United States Patent
Bulumulla et al.

(10) Patent No.: US 9,453,894 B2
(45) Date of Patent: Sep. 27, 2016

(54) SHEET OF SURFACE COILS FOR IMAGING APPLICATIONS

(75) Inventors: Selaka Bandara Bulumulla, Niskayuna, NY (US); Thomas Kwok-Fah Foo, Clifton Park, NY (US); Christopher Judson Hardy, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 1124 days.

(21) Appl. No.: 13/484,934

(22) Filed: May 31, 2012

(65) Prior Publication Data

US 2013/0320982 A1    Dec. 5, 2013

(51) Int. Cl.
*A61B 5/055* (2006.01)
*G01R 33/34* (2006.01)
*G01R 33/3415* (2006.01)

(52) U.S. Cl.
CPC ......... *G01R 33/34007* (2013.01); *A61B 5/055* (2013.01); *G01R 33/34084* (2013.01); *G01R 33/3415* (2013.01)

(58) Field of Classification Search
CPC .................... G01R 33/4084; G01R 33/34007; G01R 33/341–33/3415; G01R 33/34046
See application file for complete search history.

(56) References Cited

U.S. PATENT DOCUMENTS

| | | | | |
|---|---|---|---|---|
| 3,810,263 A * | 5/1974 | Taylor | ................... | A61G 7/1032 297/223 |
| 5,324,019 A * | 6/1994 | Chang | ................... | B65H 3/5269 271/121 |
| 6,784,665 B1 | 8/2004 | Chan et al. | | |
| 2003/0206019 A1 | 11/2003 | Boskamp | | |
| 2005/0107686 A1 | 5/2005 | Chan | | |
| 2007/0176601 A1 | 8/2007 | Adachi | | |
| 2007/0182409 A1 | 8/2007 | Varjo | | |
| 2008/0007263 A1 | 1/2008 | Machida | | |
| 2008/0129293 A1 * | 6/2008 | Schnell | ................ | A61B 5/0555 324/318 |
| 2008/0146907 A1 | 6/2008 | Koste | | |
| 2008/0197849 A1 * | 8/2008 | Heid | ................ | G01R 33/56375 324/318 |
| 2008/0246477 A1 | 10/2008 | Nakabayashi | | |
| 2010/0022867 A1 | 1/2010 | Fukuchi | | |

OTHER PUBLICATIONS

Zhang et al.; "Simultaneous Imaging Method Using Phased Array in MRI"; 2002 3rd International Conference Microwave and Millimeter Wave Technology Proceedings; Issue Date :Aug. 17-19, 2002; Pages(s): 501-504.

* cited by examiner

*Primary Examiner* — Serkan Akar
(74) *Attorney, Agent, or Firm* — Melissa K. Dobson

(57) ABSTRACT

An imaging system is presented. The imaging system includes a storage structure that stores a first sheet of coils inside a cradle, wherein the storage structure includes a plurality of first set of rotatable bodies and a plurality of second set of rotatable bodies, and a plurality of springs that are coupled to one or more of the plurality of second set of rotatable bodies, wherein the first sheet of coils is disposed around the plurality of first set of rotatable bodies, the plurality of second set of rotatable bodies and the plurality of springs, and wherein a first end of the first sheet of coils protrudes out of the cradle.

21 Claims, 9 Drawing Sheets

SHEET OF SURFACE COILS FOR IMAGING APPLICATIONS

BACKGROUND

In just a few decades, the use of magnetic resonance imaging (MRI) scanners has grown tremendously. MRI scans are being increasingly used to aid in the diagnosis of multiple sclerosis, brain tumors, torn ligaments, tendonitis, cancer, strokes, and the like. As will be appreciated, MRI is a non-invasive medical test that aids physicians in the diagnoses and treatment of various medical conditions. The enhanced contrast that an MRI scan provides between the different soft tissues of the body allows physicians to better evaluate the various parts of the body and determine the presence of certain diseases that may not be assessed adequately with other imaging methods such as X-ray, ultrasound, or computed tomography (CT).

An MRI system typically includes one or more coils to generate the magnetic field. Additionally, the MRI system also includes one or more MRI receiver coils configured to detect signals from a gyromagnetic material within a patient. The MRI receiver coils, hereinafter 'receiver coils', are used for patients of various sizes and shapes. Typically, the same sheet of receiver coils is used for patients of various sizes. The usage of the same sheet of receiver coils for patients of various sizes may either result in discomfort of the patients or inferior quality images. For example, the loosely fitting sheet of receiver coils may result in poor image quality and the tightly body hugging sheet of receiver coils may result in anxiety of a patient. Sometimes multiple sheets of receiver coils of various sizes may be maintained by imaging users for patients of different sizes. However, maintaining the multiple sheets of receiver coils adds to the cost of imaging and requires additional selection and installation time. Furthermore, the selected receiver coils may not fit a patient adequately.

BRIEF DESCRIPTION

An imaging system is presented. The imaging system includes a storage structure that stores a first sheet of coils inside a cradle, wherein the storage structure includes a plurality of first set of rotatable bodies and a plurality of second set of rotatable bodies, and a plurality of springs that are coupled to one or more of the plurality of second set of rotatable bodies, wherein the first sheet of coils is disposed around the plurality of first set of rotatable bodies, the plurality of second set of rotatable bodies and the plurality of springs, and wherein a first end of the first sheet of coils protrudes out of the cradle.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, imaging systems that use adaptable sheet of coils for imaging patients of varied sizes and geometries are presented. The imaging systems store the sheet of coils inside a cradle, and a requisite expanse of the sheet of coils may be pulled out based upon a unique size, a unique geometry and an anatomical region of a patient. In one embodiment, the word "cradle" refers to a moving part of a table. For example, in a magnetic resonance imaging system (MRI), the word "cradle", refers to a moving part of a patient's table. When a patient lies down on the cradle, the cradle may be moved inside a magnet bore to move the patient into the magnet bore for imaging. The cradle further brings out the patient at the conclusion of imaging. The patient's table, for example, may be fixed at a location. As used herein, the term "requisite expanse" is used to refer to a portion of a sheet of coils that adequately, comfortably and closely fits a patient based upon the unique size, geometry and subject anatomical region of the patient. Additionally, the cradle in the imaging systems automatically retracts the pulled out requisite expanse of the sheet of coils after completion of the imaging process. Furthermore, various embodiments of a storage structure that are used for storing the sheet of coils inside the cradle are presented. By employing the adaptable sheet of coils and the storage structure for storing the adaptable sheet of coils, the installation time required by a user (for example, a Radiologist or MR technician) for installing the sheet of coils during imaging process is reduced. Furthermore, the usage of the present systems and methods aid in getting superior image quality and a comfortable imaging experience for the patient.

Figure 1:
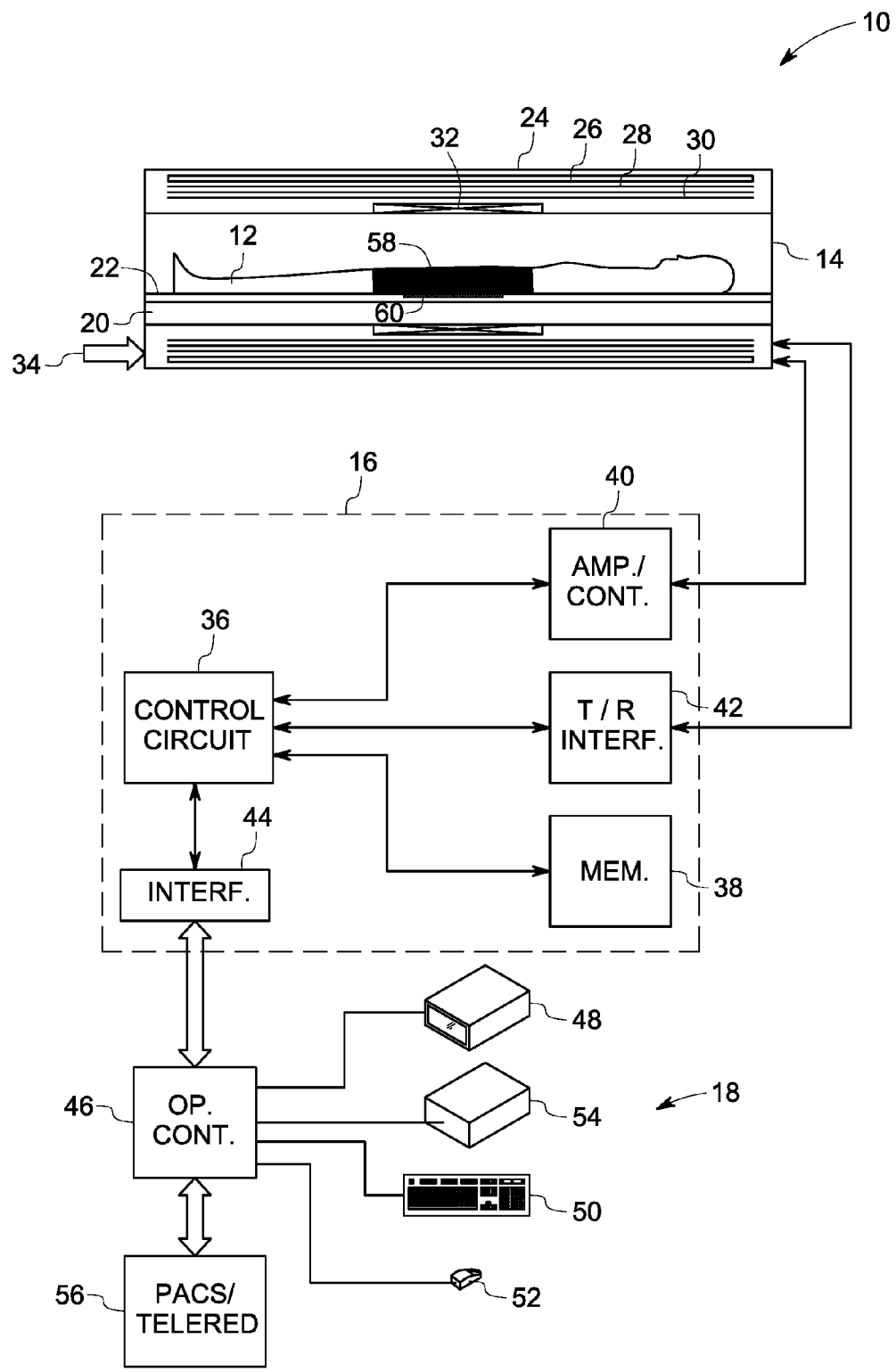
FIG. 1 is a block diagram illustration of an exemplary imaging system in the form of a magnetic resonance imaging (MRI) system configured to use the systems and methods of FIGS. 2-6.

Turning now to the drawings, and referring to FIG. 1, a block diagram of an embodiment of an MRI imaging system 10 is depicted. The MRI system 10 is illustrated diagrammatically as including a scanner 14, scanner control circuitry 16, and system control circuitry 18. While the MRI system 10 may include any suitable MRI scanner or detector, in the illustrated embodiment the system includes a full body scanner including a patient bore 20 into which a cradle 22 may be positioned to place a patient 12 in a desired position for scanning. The scanner 14 may be of any suitable field strength, including scanners varying from 0.5 Tesla to 3 Tesla field strength and beyond. As used herein, the term patient is used to refer to a human person or animal that is the subject of the imaging application. It is noted that other subjects or objects can also be imaged using the MRI imaging system.

Additionally, the scanner 14 may include a series of associated coils for producing controlled magnetic fields, for generating radio-frequency (RF) excitation pulses, and for detecting signals from gyromagnetic material within the patient 12 in response to such pulses. In the diagrammatical view of FIG. 1, a primary magnet coil 24 may be provided for generating a primary magnetic field generally aligned with patient bore 20. A series of gradient coils 26, 28 and 30 may be grouped in a coil assembly for generating controlled magnetic gradient fields during examination sequences as will be described in greater detail hereinafter. A RF coil 32 may be provided for generating radio frequency pulses for exciting the gyromagnetic material. In the embodiment illustrated in FIG. 1, the coil 32 also serves as a receiving coil. Thus, the RF coil 32 may be coupled with driving and receiving circuitry in passive and active modes for receiving signals from the gyromagnetic material and for applying RF excitation pulses, respectively. Alternatively, various configurations of receiving coils may be provided separate from the RF coil 32. Such coils may include structures specifically adapted for target anatomies, such as head coil assemblies, and so forth. Moreover, receiving coils may be provided in any suitable physical configuration, including phased array coils, and so forth.

In a presently contemplated configuration, the gradient coils are identified by 26, 28 and 30. As will be appreciated by those skilled in the art, the coils include conductive wires, bars or plates that are wound or cut to form a coil structure that generates a gradient field upon application of control pulses as described below. The placement of the coils within the gradient coil assembly may be done in several different orders. In one embodiment, a Z-axis coil may be positioned at an innermost location, and may be formed generally as a solenoid-like structure that has relatively little impact on the RF magnetic field. Thus, in the illustrated embodiment, the gradient coil 30 is the Z-axis solenoid coil, while coils 26 and 28 are Y-axis and X-axis coils respectively.

The coils of the scanner 14 may be controlled by external circuitry to generate desired fields and pulses, and to read signals from the gyromagnetic material in a controlled manner. As will be appreciated by those skilled in the art, when the material, typically bound in tissues of the patient 12, is subjected to the primary field, individual magnetic moments of the paramagnetic nuclei in the tissue partially align with the field. While a net magnetic moment is produced in the direction of the polarizing field, the randomly oriented components of the moment in a perpendicular plane generally cancel one another. During an examination sequence, an RF frequency pulse is generated at or near the Larmor frequency of the material of interest, resulting in rotation of the net aligned moment to produce a net transverse magnetic moment. This transverse magnetic moment precesses around the main magnetic field direction, emitting RF signals that are detected by the scanner 14 and processed for reconstruction of the desired image.

The gradient coils 26, 28 and 30 may be configured to serve to generate precisely controlled magnetic fields, the strength of which vary over a predefined field of view, typically with positive and negative polarity. When each coil is energized with known electric current, the resulting magnetic field gradient is superimposed over the primary field and produces a desirably linear variation in the Z-axis component of the magnetic field strength across the field of view. The field varies linearly in one direction, but is homogenous in the other two. The three coils have mutually orthogonal axes for the direction of their variation, enabling a linear field gradient to be imposed in an arbitrary direction with an appropriate combination of the three gradient coils.

The pulsed gradient fields perform various functions integral to the imaging process. Some of these functions are slice selection, frequency encoding and phase encoding. These functions may be applied along the X-axis, Y-axis and Z-axis of the original coordinate system or along other axes determined by combinations of pulsed currents applied to the individual field coils.

The slice select gradient determines a slab of tissue or anatomy to be imaged in the patient 12. The slice select gradient field may be applied simultaneously with a frequency selective RF pulse to excite a known volume of spins within a desired slice that precess at the same frequency. The slice thickness is determined by the bandwidth of the RF pulse and the gradient strength across the field of view.

The frequency encoding gradient is also known as the readout gradient, and is usually applied in a direction perpendicular to the slice select gradient. In general, the frequency encoding gradient is applied before and during the formation of the magnetic resonance (MR) echo signal resulting from the RF excitation. Spins of the gyromagnetic material under the influence of this gradient are frequency encoded according to their spatial position along the gradient field. By Fourier transformation, acquired signals may be analyzed to identify their location in the selected slice by virtue of the frequency encoding.

Finally, the phase encode gradient is generally applied before the readout gradient and after the slice select gradient. Localization of spins in the gyromagnetic material in the phase encode direction may be accomplished by sequentially inducing variations in phase of the precessing protons of the material using slightly different gradient amplitudes that are sequentially applied during the data acquisition sequence. The phase encode gradient permits phase differences to be created among the spins of the material in accordance with their position in the phase encode direction.

As will be appreciated by those skilled in the art, a great number of variations may be devised for pulse sequences employing the exemplary gradient pulse functions described hereinabove as well as other gradient pulse functions not explicitly described here. Moreover, adaptations in the pulse sequences may be made to appropriately orient both the selected slice and the frequency and phase encoding to excite the desired material and to acquire resulting MR signals for processing.

The coils of the scanner 14 are controlled by the scanner control circuitry 16 to generate the desired magnetic field and RF pulses. In the diagrammatical view of FIG. 1, the scanner control circuitry 16 thus includes a control circuit 36 for commanding the pulse sequences employed during the examinations, and for processing received signals. The control circuit 36 may include any suitable programmable logic device, such as a CPU or digital signal processor of a general purpose or application-specific computer. Also, the control circuit 36 may further include memory circuitry 38, such as volatile and non-volatile memory devices for storing physical and logical axis configuration parameters, examination pulse sequence descriptions, acquired image data, programming routines, and so forth, used during the examination sequences implemented by the scanner.

The interface between the control circuit 36 and the coils of the scanner 14 is managed by amplification and control circuitry 40 and by transmission and receive interface circuitry 42. The amplification and control circuitry 40 includes amplifiers for each gradient field coil to supply drive current to the field coils in response to control signals from the control circuit 36. Transmit/receive (T/R) circuitry 42 includes additional amplification circuitry for driving the RF coil 32. Moreover, where the RF coil 32 serves both to emit the RF excitation pulses and to receive MR signals, the T/R circuitry 42 may typically include a switching device for toggling the RF coil between active or transmitting mode, and passive or receiving mode. A power supply, denoted generally by reference numeral 34 in FIG. 1, is provided for energizing the primary magnet 24. Finally, the scanner control circuitry 16 may include interface components 44 for exchanging configuration and image data with the system control circuitry 18. It should be noted that, while in the present description reference is made to a horizontal cylindrical bore imaging system employing a superconducting primary field magnet assembly, the present technique may be applied to various other configurations.

The system control circuitry 18 may include a wide range of devices for facilitating interface between an operator or radiologist and the scanner 14 via the scanner control circuitry 16. In the illustrated embodiment, for example, an operator controller 46 is provided in the form of a computer workstation employing a general purpose or application-specific computer. The workstation also typically includes memory circuitry for storing examination pulse sequence descriptions, examination protocols, user and patient data, image data, both raw and processed, and so forth. Further, the workstation may further include various interface and peripheral drivers for receiving and exchanging data with local and remote devices. In the illustrated embodiment, such devices include a conventional computer keyboard 50 and an alternative input device such as a mouse 52. A printer 54 may be provided for generating hard copy output of documents and images reconstructed from the acquired data. Moreover, a computer monitor 48 may be provided for facilitating operator interface. In addition, the system 10 may include various local and remote image access and examination control devices, represented generally by reference numeral 56 in FIG. 1. Such devices may include picture archiving and communication systems, teleradiology systems, and the like.

As will be appreciated, surface coils are used to receive signals during imaging processes. Prior to imaging, coils may be disposed on or under one or more anatomical regions of a patient. In the presently contemplated configuration, a sheet of receiver coils 58 is disposed over the patient 12. For superior image quality and a comfortable imaging experience, the receiver coils 58 adequately and closely fit the patient 12. Furthermore, a second sheet of coils 60 may be disposed under the patient 12.

Figure 2:
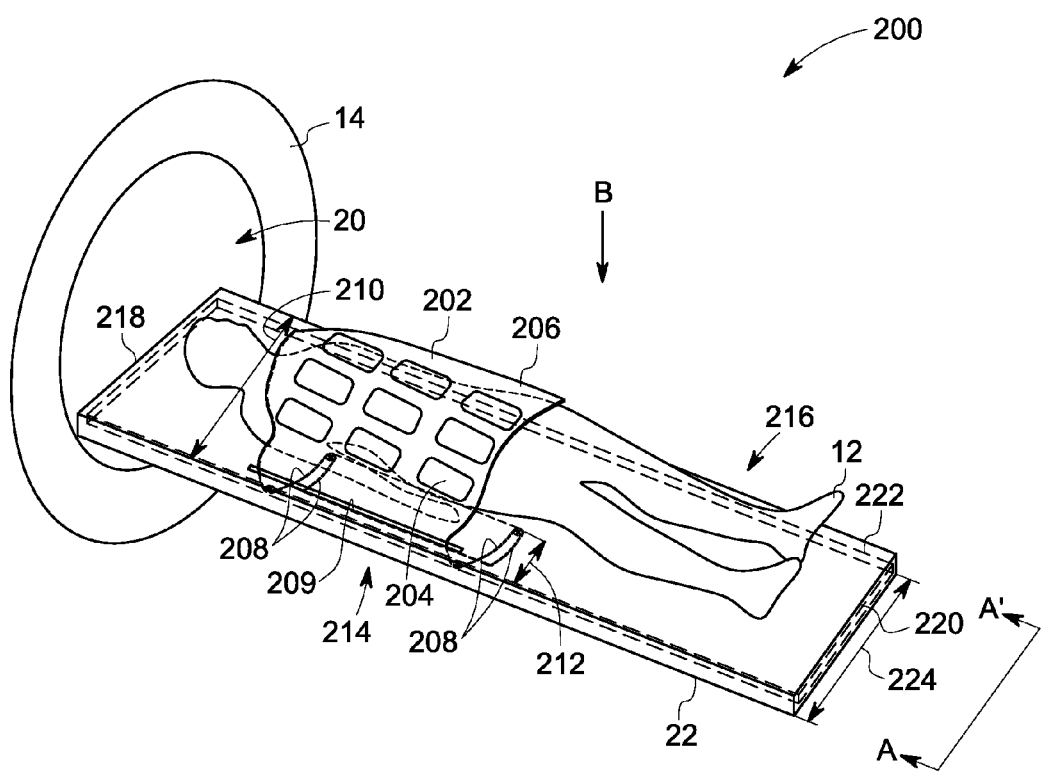
FIG. 2 is a diagrammatic illustration of a system that shows an adaptable first sheet of coils, in accordance with one embodiment of the present systems.

FIG. 2 is a diagrammatic illustration of a system 200 that shows an adaptable first sheet of coils 202, in accordance with one embodiment of the present systems. For example, the first sheet of coils 202 may be the coils 58 (shown in FIG. 1). In one embodiment, the first sheet of coils 202 may be used in the MRI 10 explained with reference to FIG. 1. The first sheet of coils 202, for example, may be a plurality of coils 204 that are disposed on/inside one or more layers of flexible substrate 206, or a rigid substrate, or combinations thereof. An example of such a sheet of coils is described in co-owned, co-pending application Ser. No. 12/977,534 entitled, "System and Method for Inductively Communicating Data," and Ser. No. 12/977,551 entitled "System and Method for Communicating Data." The plurality of coils 204, for example, may be receiver coils, transmitter coils, anterior receiver coils, posterior receiver coils, radio frequency coils, and the like. The flexible substrate 206 may be formed using a thin dielectric material such as a polyimide film or FR-4. Furthermore, the flexible substrate 206 may also incorporate a thin foam padding and/or covering, in certain embodiments. While in the presently contemplated configuration, the plurality of coils 204 are shown as being disposed on the flexible substrate 206, in certain embodiments, the plurality of coils 204 may be partially disposed on a rigid substrate (not shown) and partially on the flexible substrate 206. In one embodiment, the first sheet of coils 202 may include electrocardiography probes or ultrasound probes. In one embodiment, the first sheet of coils 202 may include one or more sensors for radio frequency catheter tracking.

In accordance with certain other aspects of the present techniques, the flexible substrate 206 is fashioned in the form of a blanket of coils. As used herein, the term blanket is used to broadly define a flexible substrate having the plurality of coils 204 that is placed on the patient 12. Also, the blanket is configured to be disposed on the patient 12 to cover the section of the patient 12 that is the focus of the scanning, examination or imaging. Also, the length and size of the blanket may be dependent upon an anatomical region of the patient 12 being scanned, examined or imaged. Particularly, the blanket may be sized such that the anatomical region of the patient 12 being scanned is adequately accommodated by the blanket. As used herein, the term "blanket" and "first sheet of coils" will be interchangeably used. While the presently contemplated configuration shows disposing the first sheet of the coils 202 over the patient 12, the first sheet of coils 202 may be disposed under the patient 12 or on any other body part of the patient 12. By way of example, if it is desirable to scan an upper region of the patient 12, then the blanket may be wrapped around the upper portion of the patient 12 or be disposed under the upper portion of the patient 12. Similarly, if a lower region of the patient 12 is being scanned, then the blanket is wrapped around the lower portion of the patient 12 or be disposed under the lower portion of the patient 12.

In the presently contemplated configuration, the system 200 is a Magnetic Resonance Imaging System, and the first sheet of coils 202 is shown as a sheet of receiver coils, however, the system 200 may be any other system and the first sheet of coils 202 may be transmitter coils. Prior to the commencement of the scanning procedure, the patient 12 is positioned on the patient cradle 22 of the imaging system 200. Subsequently the patient 12 is covered by the first sheet of receiver coils 202. Due to various sizes and geometries of patients it is desirable to have a requisite expanse of the first sheet of the receiver coils 202 that adequately covers the patient 12. Accordingly, the first sheet of receiver coils 202 is required to adequately and closely fit patients of all sizes. For example, for a bigger size patient, more expanse of the first sheet of receiver coils 202 is required. However, for a patient of smaller size, lesser expanse of the first sheet of receiver coils 202 is required.

The presently contemplated configuration shows a storage structure 208 located inside the cradle 22. The storage structure 208 stores the first sheet of the coils 202 and facilitates a user to pull out a requisite expanse of the first sheet of coils 202. The requisite expanse of the first sheet of the coils 202, for example, may be pulled out based upon the size of the patient 12 or the anatomical region to be scanned, imaged or examined. For example, in the presently contemplated configuration, a first portion 210 of the first sheet of coils 202 is used to adequately cover the patient 12. It is noted that the first portion 210 is a requisite expanse of the first sheet of the coils 202 that is required to adequately and comfortably cover the patient 12. A second portion 212 of the first sheet of the coils 202 remains stored inside the cradle 22. The storage structure 208, for example, may be a spring load arrangement, a pleated or Venetian blind arrangement, a drum, or the like. Embodiments of the storage structure are explained with reference to FIG. 3a, FIG. 3b, FIG. 4a and FIG. 4b.

The first sheet of coils 202 is stored by the storage structure 208 such that a first end (not shown in FIG. 2, shown in FIG. 3a) of the first sheet of coils 202 protrudes out of a first edge 214 of the cradle 22. The first end, for example, protrudes out of a slit 209 located on the upper surface and near the first edge 214 of the cradle 22. In one embodiment, a second end (not shown in FIG. 2, shown in FIG. 3a) of the first sheet of coils 202 is coupled to another structure (not shown in FIG. 2). The another structure, for example, may be a feeder, a mixer, a preamplifier, a fixed structure, an immovable structure, or combinations thereof. In one embodiment, the storage structure 208 extends inside the cradle 22 from the first edge 214 until a second edge 216 inside the cradle 22. As shown in FIG. 2, in one embodiment, the storage structure 208 is located inside and along the width 224 of the cradle 22. The location of the storage structure 208, for example, may be based upon the anatomical region to be scanned, imaged or examined. For example, in one embodiment, when upper body portion of the patient 12 is scanned, the storage structure 208 may be located near a top edge 218 of the cradle 22. Also, when the lower body portion of the patient 12 is to be scanned, the storage structure 208 may be located near a bottom edge 220 of the cradle 22. In one embodiment, the location of the storage structure 208 may be varied in between the top edge 218 and the bottom edge 220 based upon the body portion of the patient 12 to be scanned. In one embodiment, the storage structure 208 is located near the bottom edge 220 such that an end of the first sheet of coils 202 protrudes out of the bottom edge 220 of the cradle 22. In one embodiment, the storage structure 208 may move from respective location. Accordingly, the storage structure 208 may be moved from a first location to a second location based upon an anatomical region of the patient 12 to be imaged. For example, when the torso of the patient 12 is imaged, the storage structure 208 may be moved near the top edge 218 or in the middle of the cradle 22. In still another embodiment, the storage structure 208 may store multiple sheets of coils. The storage structure 208, for example, may store the multiple sheets of coils in series along the edge of the cradle 22. Furthermore, one or more of the multiple sheets of coils may be pulled out based upon the expanse and number of anatomical regions of the patient 12 to be imaged.

The system 200 further includes a second sheet of coils (e.g. posterior coil array) 222 that may be disposed under the cradle 22, over the cradle 22 or inside the cradle 22. The second sheet of coils 222, for example, may be the second sheet of coils 60 (see FIG. 1). In the presently contemplated configuration, the second sheet of coils 222 is disposed inside the cradle 22 as shown by dashed lines. The second sheet of coils 222, for example, may be a plurality of coils (not shown) that are disposed on a flexible substrate, or a rigid substrate, or combinations thereof. The plurality of coils, for example, may be receiver coils, transmitter coils, anterior receiver coils, posterior receiver coils, radio frequency coils, and the like.

Figure 3A:
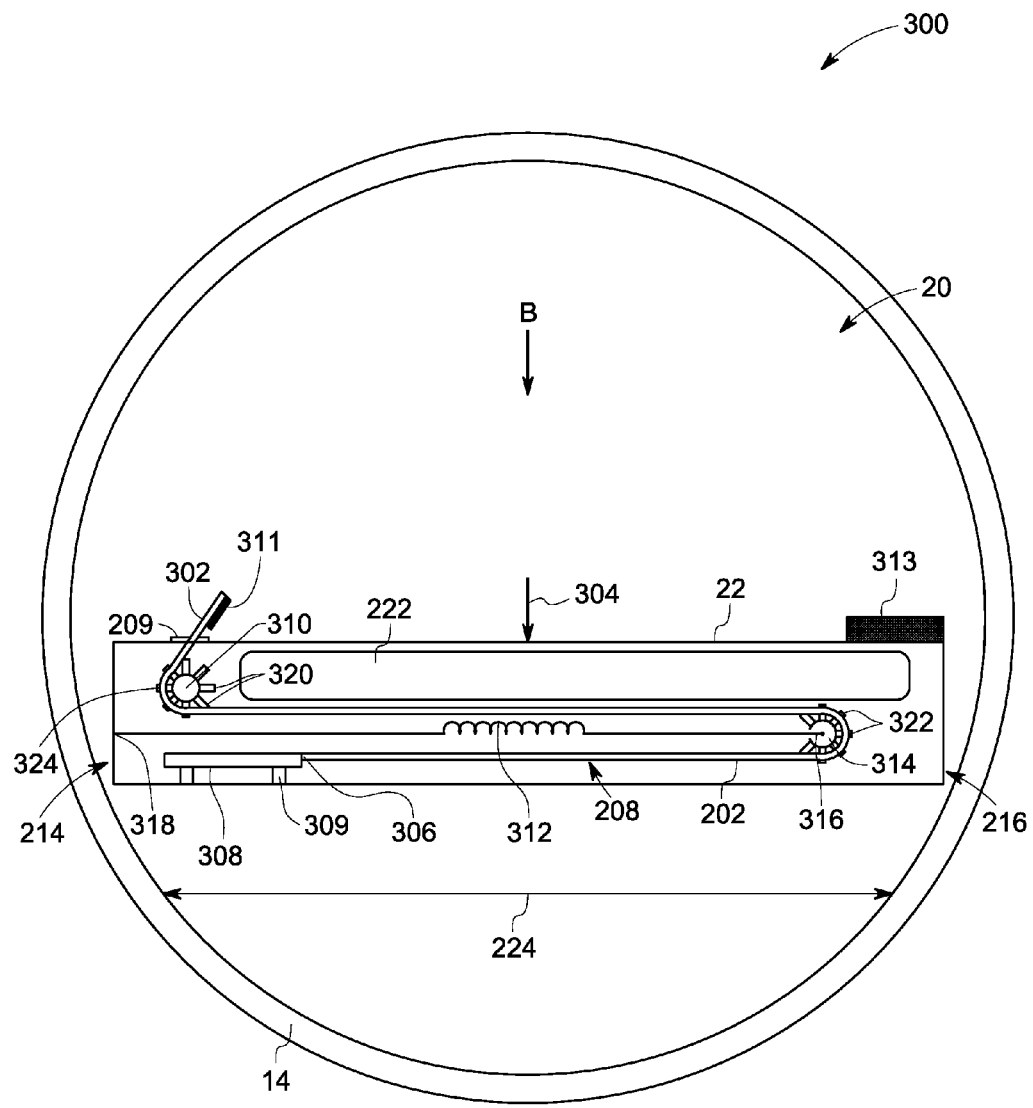
FIG. 3a is a cross-sectional view of a cradle with a storage structure shown in FIG. 2, in accordance with an embodiment of the present systems.

Moving now to FIG. 3a, a cross-sectional view 300 of the cradle 22 when viewed from the direction AA' in FIG. 2, in accordance with one embodiment of the present systems, is presented. The cross-sectional view 300 shows storage of the first sheet of coils 202. Additionally, the cross-sectional view 300 shows an embodiment of the storage structure 208. In the presently contemplated configuration, the storage structure 208 is a spring load arrangement. In the presently contemplated configuration, the entire expanse of the first sheet of coils 202 is showed as being stored by the storage structure 208, and no portion of the first sheet of coils 202 is shown as being pulled out.

As shown in FIG. 3a, the spring load arrangement 208 stores the first sheet of coils 202 inside the cradle 22 in an S-shape. As previously noted with reference to FIG. 2 and shown in FIG. 3a, a first end 302 of the first sheet of coils 202 protrudes out of the cradle 22 through the slit 209. In this embodiment, the slit 209 is located near the first edge 214 and on the top surface 304 of the cradle 22. Furthermore, as previously noted with reference to FIG. 2 and shown in FIG. 3a, a second end 306 of the first sheet of coils 202 is coupled to another structure 308. In the presently contemplated configuration, the another structure 308 is a feed board. The feed board 308, for example, includes a preamplifier, a mixer, or the like. The fixed coupling of the second end 306 of the first sheet of coils 202 to the feed board 308 includes physical coupling of the internal wires of the plurality of coils 204 (see FIG. 2) in the first sheet of coils 202 to the preamplifier, or the mixer. Furthermore, the fixed coupling of the first sheet of coils 202 includes a fixed coupling of the flexible substrate 206 (see FIG. 2) to a surface of the feed board 308. In the presently contemplated configuration, the feed board 308 is coupled to a fixed structure 309 that is coupled to the cradle 22. Since the fixed structure 309, is fixed and immovable relative to the cradle 22, the feed board 308 and the second end 306 of the first sheet of coils 202 are fixed relative to the cradle 22. It is noted that the fixed structure 309 may travel with the cradle 22 when moving the patient 12 into and out of the magnet and may be connected by cables that run on cable tracks to stationary connections.

As previously noted, the first end 302 of the first sheet of coils 202 protrudes out of the slit 209. The first end 302, for example, may be made of a rigid substrate or a flexible substrate. The first end 302, for example, is used to hold and pull out a portion of the first sheet of coils 202 by a user (not shown). The portion of the first sheet of coils 202, for example, may be the first portion 210 (shown in FIG. 2) or a requisite expanse that is used for covering an anatomical region of the patient 12. Subsequent to covering the anatomical region of the patient 12, the user (not shown) may fasten the first end 302 on a surface near the second edge 216 of the cradle 22. The user, for example, may fasten the first end 302 near the second edge 216 using a fastener. In one embodiment, the first end 302 may have one or more fasteners. The fasteners on the first end 302, for example, may be one or more latch like structures. It is noted that any suitable fastening arrangement may be used. In certain embodiments, a first fastener 311 may be disposed on the first end 302 and a second fastener 313 may be disposed on a surface near the second edge 216 of the cradle 22. The first fastener 311 and the second fastener 313 may be fastened to one another to attach the first end 302 to the surface near the second edge 216 of the cradle 22. The first fastener 311, and the second fastener 313, for example, may include a hook and loop strip, non-metallic snap-on buttons, or the like. Subsequent to the fastening of the first end 302 to the surface near the second edge 216 of the cradle 22, any extra portion of the first sheet of coils 202 that has been pulled out by the user is retracted by the storage structure 208 leaving a requisite expanse over the patient 12. Accordingly, the requisite expanse closely and comfortably fits the patient based upon the size and geometry of the patient.

Figure 4A:
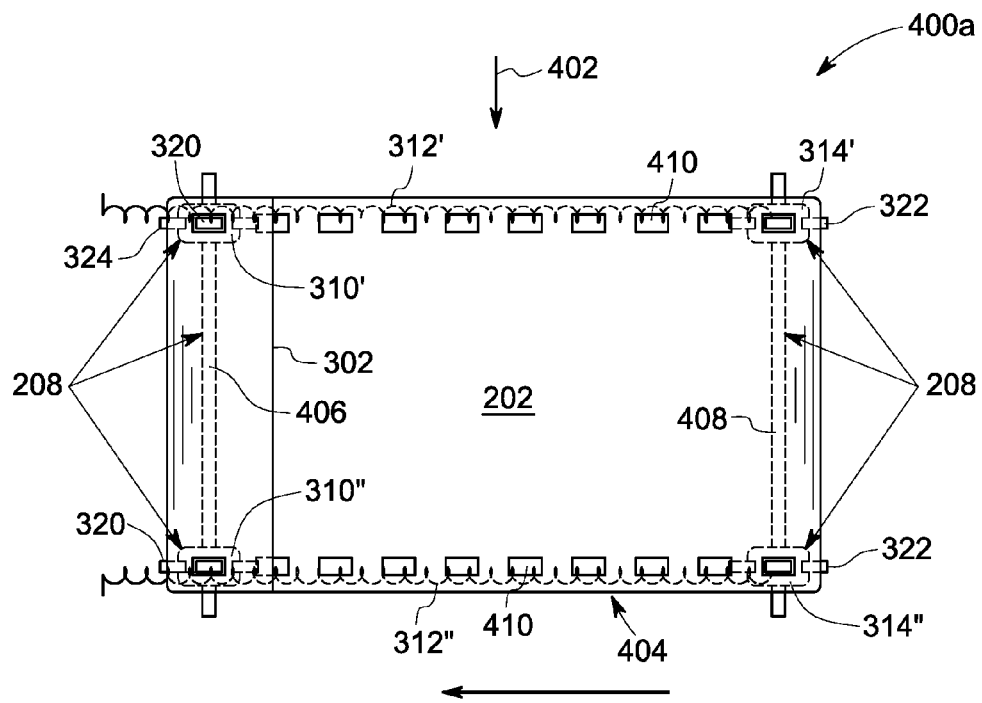
FIG. 4a shows a perspective top view of a storage structure with a first sheet of coils, in accordance with one aspect of the present systems and techniques.

As shown in FIG. 3*a*, the first sheet of coils 202 is stored by the storage structure 208 such that the first sheet of coils 202 is disposed around a plurality of first set of rotatable bodies 310, a plurality of springs 312 and a plurality of second set of rotatable bodies 314 to form the S-shape. As used herein, the term "set" is used to refer to a single rotatable body. The terms "first set" and "second set" are used herein to differentiate the plurality of first set of rotatable bodies 310 from the plurality of second set of rotatable bodies 314. It is noted that in one embodiment, the plurality of first set of rotatable bodies 310 may be a single rotatable body. Furthermore, it is noted that in one embodiment the plurality of second set of rotatable bodies 314 may be a single rotatable body. As used herein, the term "first set of rotatable bodies" and the term "second set of rotatable bodies" refer to bodies or objects that are capable of rotating. The first set of rotatable bodies 310 and the second set of rotatable bodies 314, for example, include a wheel, a sphere, a cylinder, or the like. Hereinafter, the terms "rotatable body/bodies" and "wheel/wheels" will be used interchangeably. It is noted that while the storage structure 208 has the plurality of first set of rotatable bodies 310, the plurality of springs 312 and the plurality of second set of rotatable bodies 314, the present view being a cross-sectional view 300 shows the single first set wheel 310, the single spring 312 and the single second set wheel 314. A top view, when viewed from direction B, of the storage structure 208 with the first sheet of coils 202 is shown in FIG. 4*a*. In one embodiment, the plurality of first set of wheels 310 are parallel to each other. Furthermore, in one embodiment, the plurality of second set of wheels 314 are parallel to each other. Additionally, in one embodiment, the plurality of springs 312 are parallel to each other.

As shown in FIG. 3*a*, the plurality of first set of rotatable bodies 310 is located near the first edge 214 and under the slit 209. In one embodiment, each of the first set of rotatable bodies 310 are fixed at respective locations and do not move from respective locations. However, each of the first set of rotatable bodies 310 may rotate around respective axis of rotation. In one embodiment, the plurality of first set of rotatable bodies 310 are coupled to a first axle shaft (shown in FIG. 4*a*). It is noted that when the plurality of first set of rotatable bodies 310 is a single rotatable body, then the plurality of first set of rotatable bodies 310 are not connected by the first axle shaft. It is further noted that when the plurality of second set of rotatable bodies 314 is a single rotatable body 314, then the plurality of second set of rotatable bodies 314 are not connected by the second axle shaft. The plurality of first set of rotatable bodies 310, for example, is fixedly coupled to the first axle shaft. Therefore, the first set of rotatable bodies 310 and the first axle shaft may rotate in unison around respective axis of rotation. One end (not shown) of the first axle shaft is fixedly coupled to one edge (not shown) of the cradle 22, and another end (not shown) of the first axle shaft is fixedly coupled to another end (not shown) of the cradle 22. The fixed coupling of the one end and another end of the first axle shaft with the one end and another end of the cradle 22 may include rotatable coupling. Therefore, while the first axle shaft and the first set of rotatable bodies 310 are fixed and immovable, the first axle shaft and the first set of rotatable bodies 310 may rotate around respective axis of rotation.

Figure 4B:
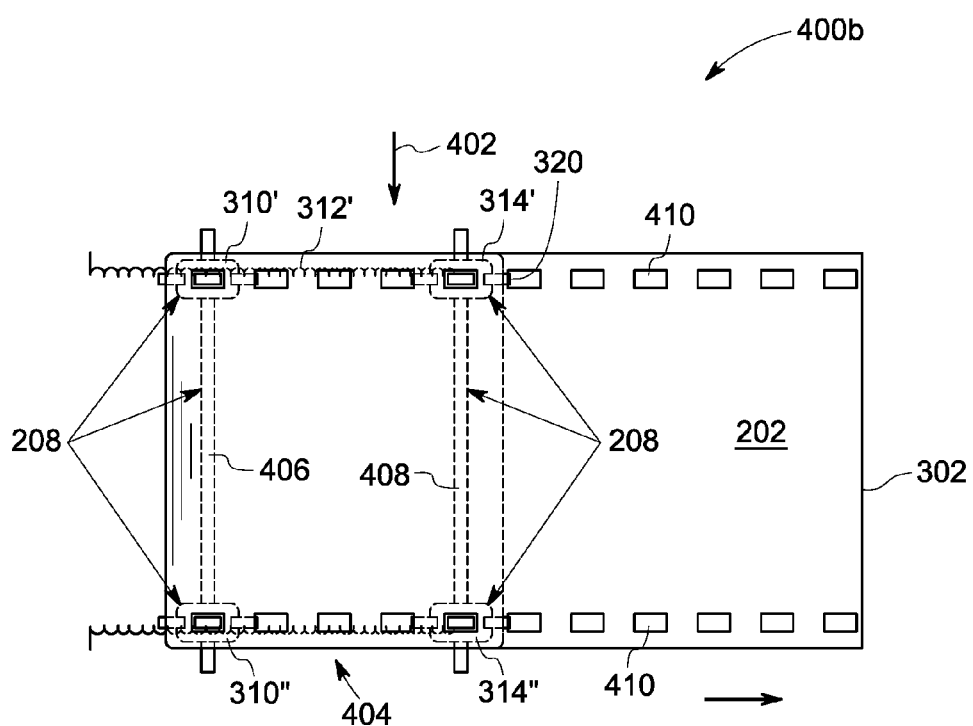
FIG. 4b shows a perspective top view of the storage structure shown in FIG. 4a when a portion of the first sheet of coils has been pulled out, in accordance with one aspect of the present systems and techniques.

Additionally, the plurality of second set of rotatable bodies 314 is located near the second edge 216 inside the cradle 22. In one embodiment, the plurality of second set of rotatable bodies 314 are coupled to a second axle shaft (shown in FIG. 4*a*). The plurality of second set of rotatable bodies 314, for example, is fixedly coupled to the second axle shaft. Therefore, the second set of rotatable bodies 314 and the second axle shaft may rotate in unison around respective axis of rotation. The second axle shaft may not be fixedly coupled with the cradle 22, and therefore the second axle shaft and the second set of wheels 314 may move from respective locations, for example, linear movement. Furthermore, in one embodiment, the second set of rotatable bodies 314 are moveably coupled to the plurality of springs 312. Accordingly, each of the second set of rotatable bodies 314 may move linearly with a motion of respective spring in the plurality of springs 312. For example, a displaced location of the second set of rotatable bodies 314 is shown in FIG. 4*b*.

Figure 3B:
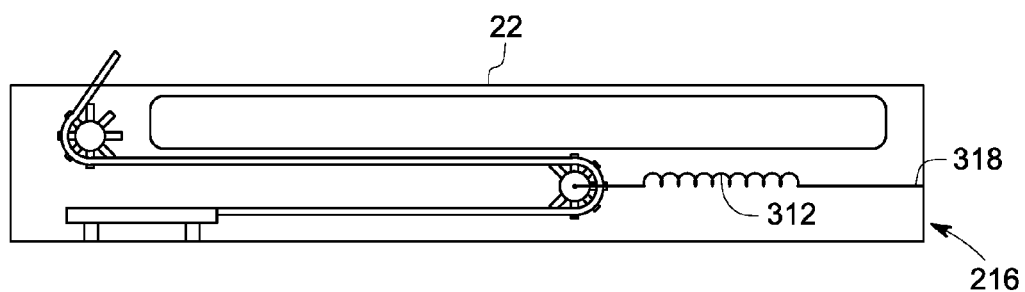
FIG. 3b is a cross-sectional view of the cradle shown in FIG. 2, in accordance with another embodiment of the present systems.

In one embodiment, a first end 316 of one or more of the springs 312 is fixedly coupled to a respective second set wheel in the second set wheels 314 such that the fixed coupling does not hinder rotation of the respective second set wheel. In certain embodiments, the first end 316 of one or more of the springs 312 may be coupled to the second axle shaft. Additionally, in one embodiment, a second end 318 of each of the springs 312 is fixedly coupled to the inner side of the first edge 214 of the cradle 22. However as shown in FIG. 3*b*, in certain embodiments, the second end 318 of each of the springs 312 is fixedly coupled to the inner side of the second edge 216 of the cradle 22.

In certain embodiments, the plurality of first set of rotatable bodies 310 and the plurality of second set of rotatable bodies 314 have teeth 320, 322, respectively. Furthermore, the first sheet of coils 202 has a plurality of holes (shown in FIG. 4*a*). The teeth 320, 322 penetrate through one or more of the plurality of holes (not shown in FIG. 3*a*, shown in FIG. 4*a*). For example, reference numeral 324 points to a small portion of one of the teeth 320 that protrudes out of a hole in the first sheet of coils 202.

In operation, when the first end 302 of the first sheet of coils 202 is pulled out by a user, a force is exerted on the first set of rotatable bodies 310 and the springs 312. As previously noted, the first set of rotatable bodies 310 are fixed and therefore, though the application of the force facilitates rotation of the first set of rotatable bodies 310, the force does not change the locations of the first set of rotatable bodies 310. The application of the force on the springs 312 results in contraction of each of the springs 312, and therefore, the springs 312 displace from an original state or equilibrium state (shown in FIG. 3*a*, FIG. 3*b* and FIG. 4*a*) to a contracted state (shown in FIG. 4*b*). The contraction of the springs 312 facilitates rotation and linear movement of the second set of rotatable bodies 314. The linear movement of the second set of rotatable bodies 314 displaces the second set of rotatable bodies 314 from respective original location (for example, shown in FIG. 4*a*) to respective new location (for example, shown in FIG. 4*b*). The contraction of the springs 312 and the movement of the second set of rotatable bodies 314 facilitate pulling out a portion, such as, the first portion 210 or a requisite expanse of the first sheet of the coils 202.

Furthermore, it may be noted, that pulling out the portion of the first sheet of coils 202 results in a displaced state or contracted state of the springs 312. Therefore, in one embodiment, when an external force is not applied by a user, for example, by means of a fastener, to hold the first portion 210, the first portion 210 may retract in the cradle 22 due to a restoring force that is applied by the springs 312. The restoring force, for example, may be applied by the springs 312 to regain respective original positions. Accordingly, when the first end 302 of the first portion 210 is not fastened or held using an external force, the first portion 210 retracts back in the storage structure 208.

As previously noted, FIG. 4*a* shows a perspective top view 400*a* of the storage structure 208 with the first sheet of coils 202, in accordance with one aspect of the present techniques. In the presently contemplated configuration, the storage structure 208 is the spring load arrangement in accordance with one embodiment. As previously noted with reference to FIG. 3*a*, the spring load arrangement 208 includes the plurality of first set of rotatable bodies 310, the plurality of springs 312 and the plurality of second set of rotatable bodies 314. In FIG. 4*a* reference numeral 310', 312' and 314' are used to show a first set wheel in the plurality of first set of rotatable bodies 310, a spring in the plurality of springs 312 and a second set wheel in the plurality of second set of rotatable bodies 314, respectively, that are located near the first side 402 of the first sheet of coils 202. Similarly, reference numerals 310", 312" and 314" are used to show a first set wheel in the plurality of first set of rotatable bodies 310, a spring in the plurality of springs 312 and a second set wheel in the plurality of second set of rotatable bodies 314, respectively, that are located near the second side 404 of the first sheet of coils 202.

It is noted that while the presently contemplated configuration shows two wheels 310', 310" in the first set of rotatable bodies 310 and two wheels 314', 314" in the second set of rotatable bodies 314, a number of wheels may vary based upon the size of the cradle 22. As shown in FIG. 4*a*, in one embodiment, the first set of rotatable bodies 310 including the wheels 310', 310" are coupled to one another via a first axle shaft 406. Since the wheels 310', 310" are coupled via the first axle shaft 408, both the wheels 310', 310" rotate together and complete similar number of rotations at a time instant. Similarly, the second set of rotatable bodies 314 including the wheels 314', 314" are coupled via a second axle shaft 408 to rotate together and complete similar number of rotations at a time instant. As previously noted with reference to FIG. 3*a*, the first axle shaft 406 is fixedly coupled to the cradle 22 and the second axle shaft 408 is not fixedly coupled to the cradle 22. Accordingly, the first axle shaft 406 and the wheels 310', 310" do not move from respective locations, however, the second axle shaft 408 and the wheels 314' 314" may move linearly from respective locations.

Furthermore, as previously noted with reference to FIG. 3*a* and shown in FIG. 4*a*, the first sheet of coils 202 includes a plurality of holes 410. In one embodiment, the holes 410 are located along the length and on both the sides 402, 404 of the first sheet of coils 202. Additionally, as previously noted with reference to FIG. 3*a*, each of the first set of rotatable bodies 310', 310" have the teeth 320, and the second set of rotatable bodies have the teeth 322. The teeth 320 in the first set of rotatable bodies 310', 310" and the teeth 322 in the second set of rotatable bodies 314', 314" penetrate through one or more of the holes 410. For example, as referred to and shown in FIG. 3*a* and FIG. 4*a*, the tooth 324 penetrates through a hole. The penetration of the teeth 320, 322 in one or more of the holes 410 holds the first sheet of coils 202 tightly and prevents slippage, as well as formation of wrinkles or crumples on the first sheet of coils 202. Furthermore, the penetration of the teeth 320, 322 in one or more of the holes 410 helps in maintaining a close fit for the patient 12.

It is noted that FIG. 4*a* shows a position of the storage structure 208 when the first end 302 of first sheet of coils 22 has not been pulled out for covering the patient 12. In other words, FIG. 4*a* shows a normal position of the springs 312 (312', 312") when the springs 312' 312" have neither stretched nor contracted. As stretched or contracted position of the springs 312', 312", in accordance with one embodiment is shown in FIG. 4*b*. Turning now to FIG. 4*b*, a perspective top view 400*b* of the storage structure 208 with the first sheet of coils 202 when a portion of the first sheet of coils 202 has been pulled out, in accordance with one aspect of the present systems and techniques is shown. As shown in FIG. 4*a*, when the springs 312', 312" are in respective normal positions, the wheels 314', 314" are located in respective original locations. However, as shown in FIG. 4*b*, when the first end 302 of the first sheet of coils 202 is pulled out, a force F is applied on each of the springs 312', 312" of the wheels 314', 314", respectively, results in contraction of the springs 312', 312". The contraction of the springs 312', 312" further leads to displacement of the second set of rotatable bodies 314', 314" and the second axle shaft 408 in the direction of the force. FIG. 4*b* shows contracted positions of the springs 312', 312" and displaced locations of the second set of rotatable bodies 314', 314". Particularly, FIG. 4*b* shows a top view 400*b* of the storage structure 208 when the first end 302 of the first sheet of coils 202 is pulled out. It is noted that after movement of the wheels 314', 314" from the first position (shown in FIG. 4*a*) to the second position (shown in FIG. 4*b*), the teeth 322 of the second set of rotatable bodies 314', 314" penetrates through another set of one or more of the holes 410 in the first sheet of coils 202.

Figure 5A:
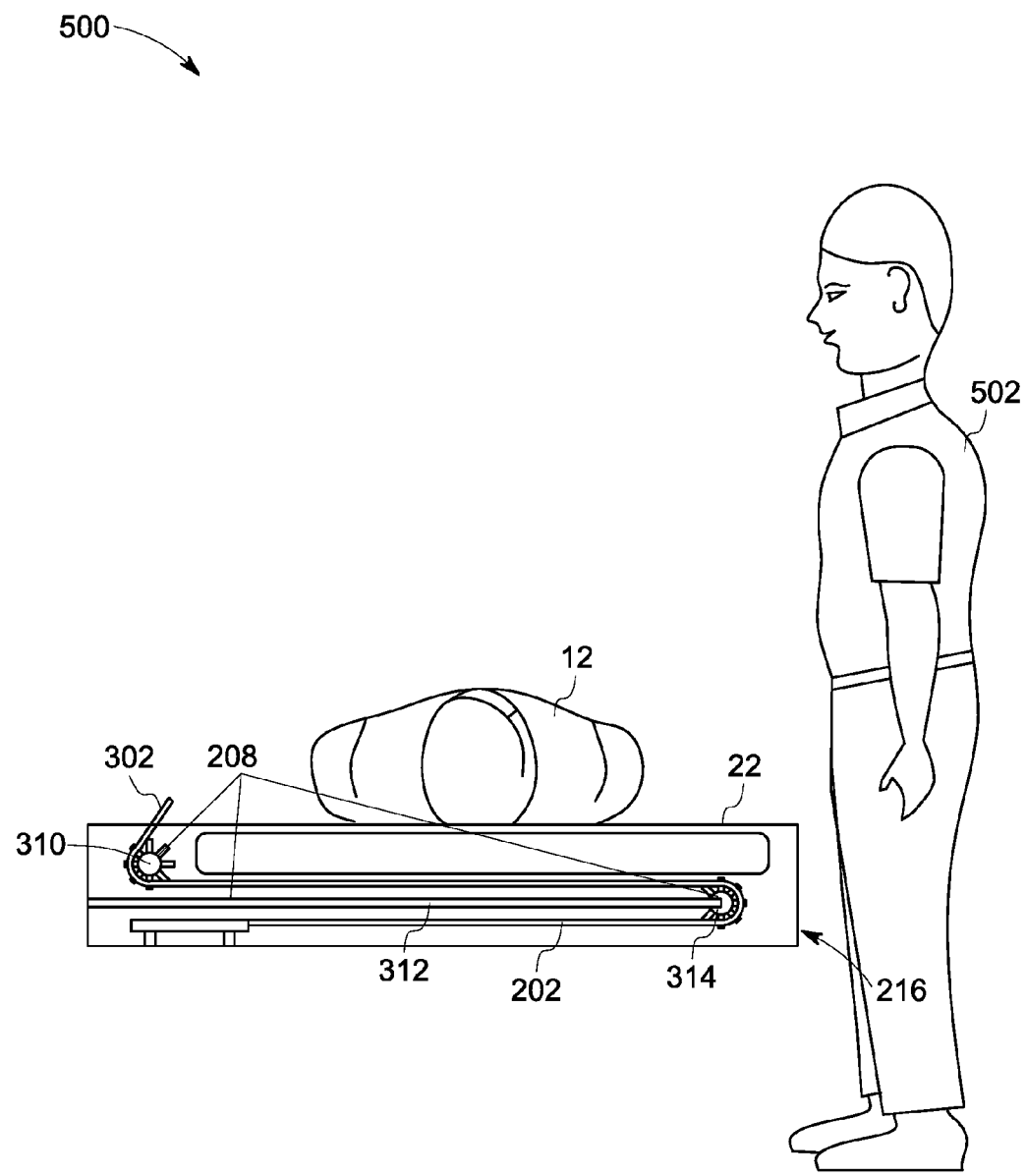
FIG. 5a, FIG. 5b and FIG. 5c are diagrammatic illustrations to show a method of operating a storage structure (workflow), in accordance with one aspect of the present systems and techniques.
Figure 5B:
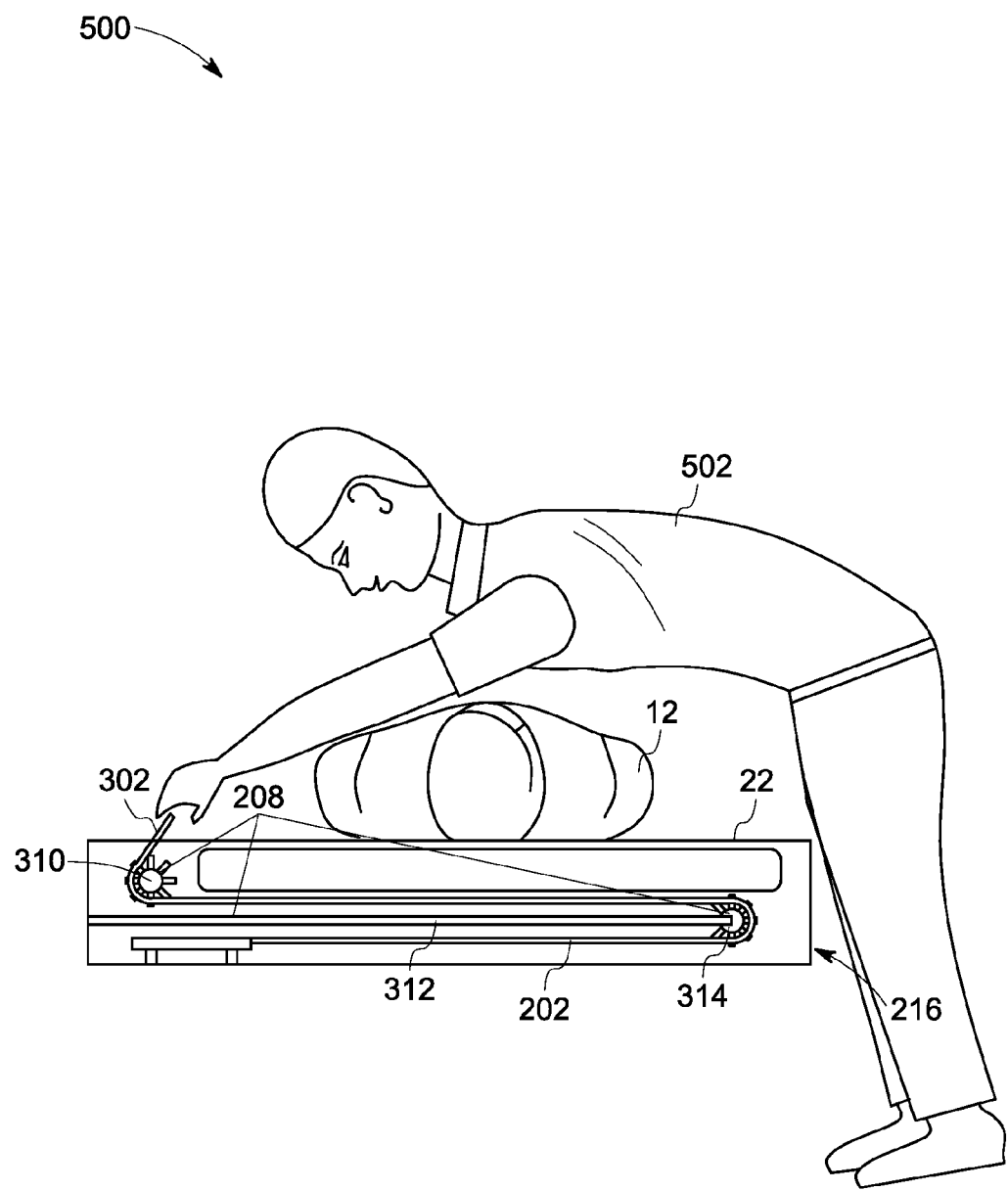
Figure 5C:
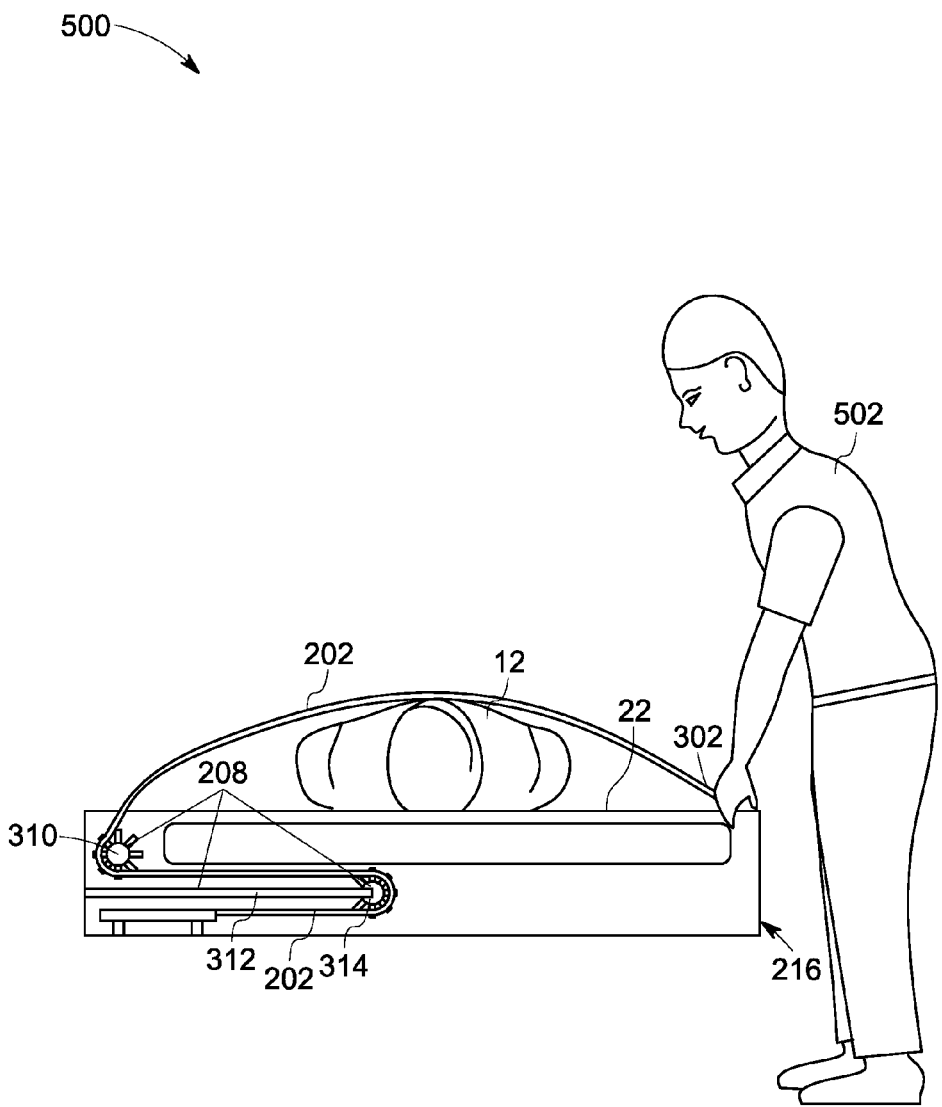

Moving now to FIG. 5*a*, FIG. 5*b* and FIG. 5*c*, a diagrammatic illustration 500 of a method of operating the storage structure 208 to pull out a portion of the first sheet of coils 202 by a user 502 is illustrated. As previously noted, the storage structure 208 includes the plurality of first set of rotatable bodies 310, the plurality of springs 312 and the plurality of second set of rotatable bodies 314. As shown in FIG. 5*a*, the storage structure 208, by default, stores the first sheet of coils 202 inside the cradle 22. When the patient 12 is to be imaged, scanned or examined by the imaging device 10 (shown in FIG. 1), the patient 12 lies down on the cradle 22. Before initiation of imaging, an anatomical region of the patient 12 to be imaged is covered by the first sheet of coils 202. For covering the anatomical region, the user 502 holds the first end 302 and pulls out a portion of the first sheet of coils 202 (shown in FIG. 5*b*). The user 502, for example, pulls out the portion of the first sheet of coils 202 based upon the size of the patient 12.

Furthermore, as shown in FIG. 5*c*, the user 502 covers the patient 12 with the pulled out portion of the first sheet of coils 202. Subsequent to covering the patient 12, the user 502 fastens the first end 302 using a fastener (not shown). As previously noted, the first end 302, for example, is fastened on the surface near the second edge 216 of the cradle 22. As noted with reference to FIG. 3*a*, the first fastener 311 may be disposed on the first end 302 and the second fastener 313 may be disposed on the surface near the second edge 216 of the cradle 22. When the first end 302 is fastened, any extra portion of the first sheet of coils 202 that has been pulled out by the user 502 is retracted by the storage structure 208 due to a restoring force applied by the springs 312. The extra portion, for example, is retracted in the cradle 22. Accordingly, a requisite portion of the first sheet of coils 202 that is required to comfortably cover the patient 12 remains over the patient 12. The adequate portion gives the patient 12 a close and comfortable fit. For example, the comfortable fit may reduce movements of the patient 12 during imaging process. Also, the closer fit may facilitate acquisition of superior quality image signals resulting in superior quality images.

Additionally, subsequent to completion of the imaging process, the first end 302 may be unfastened. For example, the first fastener 311 may be detached or unfastened from the second fastener 313. Subsequently the first end 302 may be abandoned or left by the user 502. When the user 502 abandons or leaves the first end 302, the springs 312 regain respective original positions due to restoring force. Accordingly, the requisite expanse of the first sheet of coils 202 retracts inside the cradle 22. The storage structure 208 is, therefore, configured to retract the requisite expanse of the first sheet of coils 202, such as, the first portion 210 that is not being used for covering the patient 12.

Figure 6A:
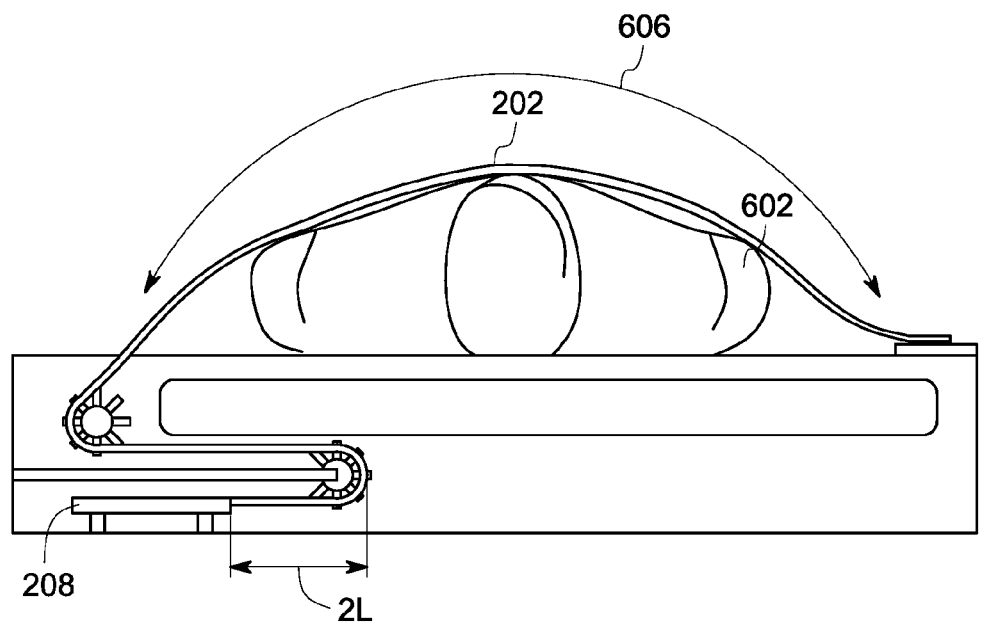
FIG. 6a and FIG. 6b are diagrammatic illustration of a storage structure to shows that a requisite expanse of a first sheet of coils varies based upon a patient size.
Figure 6B:
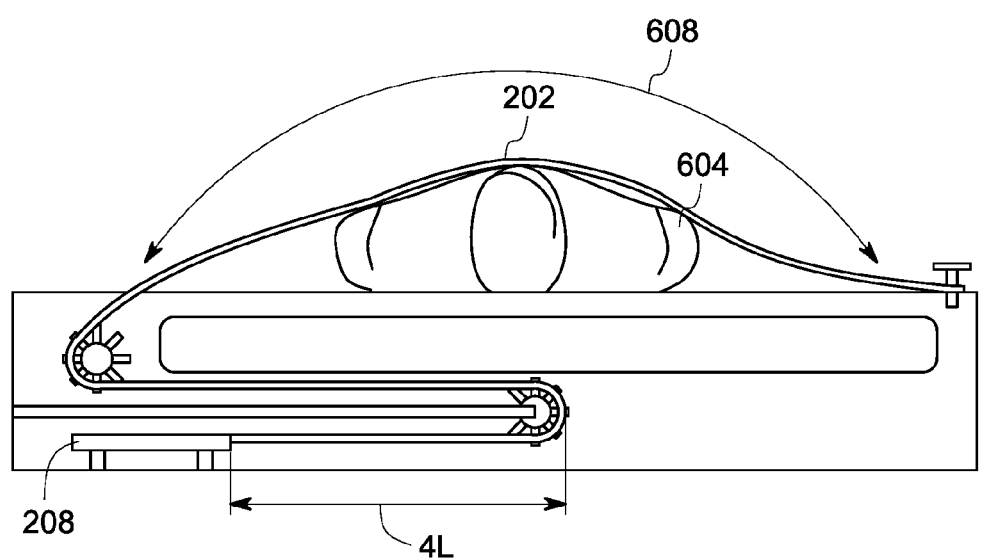

It is further noted that the requisite expanse of the first sheet of coils 202 may vary based upon the size and geometry of the patient 12. For example, as shown in FIGS. 6a and 6b, when a patient 602 is bigger in size and geometry in comparison to a patient 604, a bigger expanse 606 of the first sheet of coils 202 is required to cover the patient 602 in comparison to a smaller expanse 608 that is required to cover the smaller patient 604. It is noted from FIG. 6a and FIG. 6b that since the patient 602 requires the bigger expanse 606 of the first sheet of coils 202, a smaller portion (2L) of the first sheet of coils 202 remains stored in the storage structure 208. However, since the patient 604 requires a smaller expanse 608 of the first sheet of coils 202, a bigger expanse (4 L) of the first sheet of coils 202 remains stored in the storage structure 208.

As previously noted the first sheet of coils 202 includes the plurality of coils 204 (see FIG. 1). One or more of the plurality of coils 204 detect and acquire signals from a gyromagnetic material within the patient 12, and transmit the signals to a control circuit, such as, the control circuit 16, 36 (see FIG. 1). A number of coils in the plurality of coils 204 that cover the patient 12 may vary based upon the size and geometry of the patient 12. Accordingly, a number of coils in the plurality of coils 204 used in the acquisition of the signals from the gyromagnetic material within the patient 12 may vary based upon the size and geometry of the patient 12. For example, when a patient is bigger in size, a bigger expanse of the first sheet of coils 202 and correspondingly a larger number of coils in the plurality of coils 204 covers the patient 12. In comparison, when the patient 12 is smaller, a smaller expanse of the first sheet of coils 202 and correspondingly a smaller number of coils in the plurality of coils 204 covers the patient 12. In accordance with one embodiment of the presently contemplated configuration, a processing subsystem, such as, the control circuit 16, 26 may automatically determine a number of coils in the plurality of coils 204 that cover the patient 12. The number of coils, for example, may be determined after a pre-scan. It is noted that during a pre-scan, pre-scan signals are acquired by the plurality of coils 204. As used herein, the term "pre-scan" signals are used to refer to signals that are acquired by the plurality of coils during the conduction of pre-scan. The amplitudes of one or more of the pre-scan signals acquired by one or more coils in the coils 204 that do not cover the patient 12 may be less than one or more predetermined amplitudes. Similarly, the amplitudes of one or more of the pre-scan signals acquired by one or more coils in the coils 204 that cover the patient 12 may be higher than the one or more predetermined amplitudes. Accordingly, the amplitudes of the pre-scan signals are compared to the predetermined amplitudes to determine coils in the plurality of coils 204 that cover the patient 12 and that do not cover the patient 12. The coils in the plurality of coils 204 that cover the patient 12 may be activated for imaging, while the coils that do not cover the patient 12, may be deactivated. The comparison, activation and deactivation may be conducted by the control circuit 16, 36. The coils that do cover the patient 12 may be disabled by activating blocking circuits or turning off power to pre-amplifiers. In certain alternative embodiments, the coils that do not cover the patient 12 may not be deactivated, however, outputs/signals received from such coils that do not cover the patient 12 may be discarded.

The present systems and methods described hereinabove present an adaptable sheet of coils, such as, receiver coils for patients of various sizes. A single adaptable sheet of receiver coils (for example, an anterior array of receiver coils in MR system) closely and comfortable fits multiple patient sizes. Particularly, the adaptable sheet of coils is beneficial for pediatric imaging where children who grow very rapidly and have varied sizes are imaged. Furthermore, a user, such as, an MR technologist may operate and dispose the adaptable sheet of coils singlehandedly by standing on one side of a patient table. Since a single adaptable sheet of coils is used for patients of varied sizes, no time is spent by the user for selection of an appropriate size sheet of receiver coils. Also, since the adaptable sheet of coils fits around and embraces a patient based upon the size of the patient, installation time required for disposing adaptable sheet of coils is minimal Additionally, the adaptable sheet of coils automatically, closely and comfortable fits patients of all sizes by retracting any extra portion taken out by user. Furthermore, adaptable sheet of coils retracts inside a cradle when not in use and therefore efforts required for maintaining and storing adaptable of coils are reduced.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system, comprising:
   a magnetic resonance imaging system or a computerized tomography scanner,
   a first sheet of coils configured to cover a patient for imaging:
   a storage structure that stores the first sheet of coils inside a cradle, wherein the storage structure comprises:
   a first axle shaft and a second axle shaft:
   a plurality of first set of rotatable bodies fixedly coupled to the first axle shaft and a plurality of second set of rotatable bodies fixedly coupled to the second axle shaft; and
   a plurality of springs that are coupled to one or more of the plurality of second set of rotatable bodies,
   wherein the first sheet of coils is wrapped around the plurality of first set of rotatable bodies and the plurality of second set of rotatable bodies,
   wherein a first end of the first sheet of coils protrudes out of the cradle,
   wherein the second axle shaft and the plurality of second set of rotatable bodies are coupled to the plurality of springs to enable a linear movement of the plurality of second set of rotatable bodies and wherein the linear movement of the plurality of second set of rotatable bodies enable stretching or contraction of the plurality of springs to enable pulling out a requisite expanse of the first sheet of the coils from the storage structure.

2. The imaging system of claim 1, wherein the storage structure is disposed along a width of the cradle.

3. The imaging system of claim 1, wherein the plurality of first set of rotatable bodies comprises a drum or a wheel and the plurality of second set of rotatable bodies comprises a drum or a wheel.

4. The imaging system of claim 1, wherein the plurality of first set of rotatable bodies are disposed near a first edge of the cradle.

5. The imaging system of claim 1, wherein the plurality of first set of rotatable bodies are disposed under a slit located on a surface of the cradle.

6. The imaging system of claim 4, wherein the plurality of second set of rotatable bodies are located near a second edge of the cradle.

7. The imaging system of claim 6, wherein the plurality of first set of rotatable bodies are configured to rotate in unison with the first axle shaft and the plurality of second set of rotatable bodies are configured to rotate in unison with the second axle shaft.

8. The imaging system of claim 6, wherein a first end of the first axle shaft is fixedly coupled to one edge of the cradle and a second end of the first axle shaft is fixedly coupled to another edge of the cradle.

9. The imaging system of claim 8, wherein the first axle shaft is fixedly coupled to the cradle such that the first axle shaft and the plurality of first set of rotatable bodies do not move from respective location.

10. The imaging system of claim 6, wherein a first end of one or more of the plurality of springs is fixedly coupled to a respective second set wheel in the plurality of second set of rotatable bodies such that the fixed coupling of the plurality of springs to the respective second set wheel does not hinder rotation of the plurality of second set of rotatable bodies.

11. The imaging system of claim 10, wherein a second end of each of the plurality of springs is fixedly coupled to an inner side of the first edge or the second edge of the cradle.

12. The imaging system of claim 1, wherein the plurality of springs are located parallel to each other, the plurality of first set of rotatable bodies are located parallel to each other and the plurality of second set of rotatable bodies are located parallel to each other.

13. The imaging system of claim 1, further comprising a coupling of a second end of the first sheet of coils to another structure, comprising:
an operational coupling of the second end of the first sheet of coils to the another structure; and
a physical coupling of a flexible substrate or a rigid substrate of the first sheet of coils to the another structure.

14. The imaging system of claim 1, wherein the plurality of the first set of rotatable bodies and the plurality of the second set of rotatable bodies comprise teeth around the outer periphery.

15. The imaging system of claim 14, wherein the first sheet of coils comprises a plurality of holes.

16. The imaging system of claim 15, wherein one or more of the teeth penetrate though one or more of the plurality of holes.

17. The imaging system of claim 1, further comprising a second sheet of coils that are disposed inside the cradle or on the cradle.

18. The imaging system of claim 17, wherein the storage structure is located under the second sheet of coils.

19. The imaging system of claim 1, wherein the first sheet of coils comprises a plurality of coils that are disposed on one or more layers of a flexible substrate, a rigid substrate, or combinations thereof.

20. The imaging system of claim 19, wherein the plurality of coils comprises a receiver coil, a transmitter coil, an anterior receiver coil, a posterior receiver coil, a radio frequency coil, or combinations thereof.

21. An imaging system, comprising:
a magnetic resonance imaging system or a computerized tomography scanner,
a first sheet of coils configured to cover a patient for imaging;
a storage structure that stores the first sheet of coils inside a cradle, wherein the storage structure comprises:
a first axle shaft and a second axle shaft:
at least a first rotatable body fixedly coupled to the first axle shaft and at least a second rotatable body fixedly coupled to the second axle shaft; and
at least one spring that is coupled to the at least second rotatable body,
wherein the first sheet of coils is wrapped around the at least first rotatable body and the at least second rotatable body;
wherein a first end of the first sheet of coils protrudes out of the cradle,
wherein the second axle shaft and the at least second rotatable body are coupled to the at least one spring to enable a linear movement of the at least second rotatable body, and wherein the linear movement of the at least second rotatable body enable stretching or contraction of the at least one spring to enable pulling out a requisite expanse of the first sheet of the coils from the storage structure.

* * * * *